(12) United States Patent
Faran

(10) Patent No.: US 8,961,897 B2
(45) Date of Patent: Feb. 24, 2015

(54) DISPOSABLE MEASURING DEVICE FOR UV RADIATION

(75) Inventor: Ori Faran, Haifa (IL)

(73) Assignee: Skyrad Ltd., Nesher (IL)

( * ) Notice: Subject to any disclaimer, the term of this patent is extended or adjusted under 35 U.S.C. 154(b) by 413 days.

(21) Appl. No.: 12/918,981

(22) PCT Filed: Feb. 22, 2009

(86) PCT No.: PCT/IL2009/000200
§ 371 (c)(1),
(2), (4) Date: Aug. 23, 2010

(87) PCT Pub. No.: WO2009/104192
PCT Pub. Date: Aug. 27, 2009

(65) Prior Publication Data
US 2010/0329950 A1 Dec. 30, 2010

Related U.S. Application Data

(60) Provisional application No. 61/030,813, filed on Feb. 22, 2008.

(51) Int. Cl.
*G01N 21/75* (2006.01)
*G01J 1/50* (2006.01)
*G01N 33/52* (2006.01)

(52) U.S. Cl.
CPC . *G01J 1/50* (2013.01); *G01N 21/75* (2013.01); *G01N 33/52* (2013.01)

USPC .................................................. 422/425

(58) Field of Classification Search
CPC .......... A61Q 17/00; G01J 1/38; B41M 5/136; G01T 1/02; G01N 31/22; G01N 21/75; G01N 33/52
USPC .................................................. 422/425
See application file for complete search history.

(56) References Cited

U.S. PATENT DOCUMENTS

| | | | |
|---|---|---|---|
| 3,903,423 A | | 9/1975 | Zweig |
| 4,521,793 A | * | 6/1985 | Kabashima et al. .......... 503/201 |
| 4,857,438 A | * | 8/1989 | Loerzer et al. ................ 430/332 |
| 5,605,230 A | | 2/1997 | Marino et al. |
| 5,880,063 A | * | 3/1999 | Hoffman et al. .............. 503/201 |
| 6,130,435 A | | 10/2000 | Rocklin |
| 6,132,681 A | | 10/2000 | Faran et al. |
| 6,504,161 B1 | | 1/2003 | Jackson et al. |
| 2006/0145091 A1 | * | 7/2006 | Patel .......................... 250/474.1 |
| 2007/0172951 A1 | * | 7/2007 | Levy et al. ........................ 436/5 |

* cited by examiner

*Primary Examiner* — Lore Jarrett
(74) *Attorney, Agent, or Firm* — Browdy and Neimark, PLLC

(57) ABSTRACT

A disposable device for measuring UV radiation comprising: a matrix, at least one photochrome compound provided to said matrix wherein said photochromic compound is capable of changing its color when exposed to UV radiation, color changing agent distributed within said matrix, wherein said color changing agent irreversibly changes the device's color as a function of the UV dose irradiated, whereby said device is not affected by ambient conditions and visible light.

14 Claims, 4 Drawing Sheets

DISPOSABLE MEASURING DEVICE FOR UV RADIATION

This present application claims the benefit of earlier U.S. Provisional Patent Application Ser. No. 61/030,813 filed on Feb. 22, 2008 by Faran Ori and entitled "Disposable Measuring Device for US Radiation".

FIELD OF THE INVENTION

The present invention relates to radiation protection. More particularly, the present invention relates to an improved disposable, simple, cheap, and convenient device, which is suitable for personal protection from the sun or for industrial, agriculture and anti counterfeiting applications.

BACKGROUND OF THE INVENTION

The ultraviolet region (UV region) is a region of the electromagnetic spectrum adjacent to the low end of the visible spectrum. The UV region extends between 100-400-nm, and is divided into 3 sub regions: the UVA region (320-400-nm), the UVB region (280-320-nm), and the UVC region (100-280-nm).

In the last three decades, the levels of UV radiation that reach the earth have increased substantially due to the depletion of the ozone layer, caused by the release of various chemicals in the form of aerosols into the atmosphere.

In some parts of the world, the level of UV radiation has increased by 30-50%. The consequence of this process is a substantial increase in the danger of exposure to the sun's radiation.

It is believed, for example, that every 1% increase in the level of UV radiation corresponds to a 4% increase in the number of skin cancer cases. Indeed, according to medical statistics the number of skin cancer cases has increased by hundreds of percents in the last 20 years.

Of the three regions, the exposing to radiation in the UVB region is considered to be the most dangerous to human beings, since it causes several types of the must common cancer in human beings, i.e. skin cancer. One of the types of this cancer, namely melanoma, is lethal. In addition to the above, exposure to radiation in the UVB region can cause skin aging and is also harmful to eyes.

Radiation in the UVA region mainly causes damage, such as photo-aging, to the skin. Radiation in the UVC region does not penetrate the ozone layer, but is used in some industrial applications.

UV radiations also cause damage to agriculture crofts, plants, polymer and fabric made products.

On the other hand, artificial UV radiations is been used to cure printed ink, purify water, in semi conductors industry etc. In these cases there is a need to know the dose of exposure in order to prevent damage or to insure that the process will be successful.

Another application is using the irreversibility color change of the new device after exposure to UV from the sun or from artificial sources, in order to alert user if a package to which the device was attach/combine was open, or to confirm its originality by exposing the covered attached/combined device on the package to UV radiation and observe the irreversible color change.

In humans, UV radiation induces biological effects depending on the particular wavelength of the radiation. It is known to evaluate total biological or hazard weighted irradiation by multiplying the spectral irradiation at each wavelength by the biological or hazard weighted factor and then summation results of the multiplying over all the wavelengths.

Biological or hazard factors are obtained from the so-called action spectrum according to Environmental health criteria 160 "Ultraviolet radiation" issued by the World Health Organization, Geneva, 1994. An action spectrum is a graph of the reciprocal of the radiant exposure required to produce the given harmful effect at each wavelength. All the data in such graphs are normalized to the datum at the must efficacious wavelength. By summation of the biologically effective irradiation over the exposure period, the biologically effective radiant exposure (efficacy in J/m.sup.2) can be calculated.

The action spectrum graph for UV induced erythema was adopted worldwide by many organizations such as:
1. ACGIH (American Conference of Governmental Industrial Hygienists)
2. WHO (World Health Organization)
3. UNEP (United Nations Environment Program)
4. INIRC (International Non Ionizing Radiation Committee)

The action spectrum graph is a complex curve, obtained by statistical analysis of many research results establishing the minimum radiant exposure to the UV radiation at different wave lengths sufficient for causing erythema.

The most commonly used quantity of radiation associated with the erythemal potential due to exposure to UV radiation is the number of so-called minimum erythemal doses (MED) caused by the exposure. An MED is defined as the radiant exposure of the UV radiation that produces a just noticeable erythema on previously unexposed skin. The radiant exposure to monochromatic radiation at around 300 nm with the maximum spectral efficacy, which is required for erythema corresponds to approximately 200 to 2000 J/m. ^0.2 efficacy, depending on the skin type.

The skin reacts to radiation by changes in the melanin content. Subsequent to the change in the melanin content reddening occurs, and then soreness and signs of sun burning appear.

There exist 5 skin types that differ according to the color of human hair, eyes, and skin, and by their reaction to overexposure to UV radiation. The permissible time for exposure to UV radiation on a mid summer day changes from 15 minutes for skin type no. 1, to about 2 hours for skin type no. 5 (without using sun screen).

Most people are not aware of the danger that can arise even after limited exposure to UV radiation, because the dose is accumulated during the exposing for varying periods of time in a daily life routine. The first visible sign is usually sunburn, which might only become visible after a few hours. This means that the individual becomes aware of the danger only after the damage has already been done. It should be emphasized that skin cancer might even appear years later.

Unfortunately, most people routinely do not use sun screens unless they are on the beach or a trip. Even then, people usually do not use means of protection before they become exposed to the sun's radiation, and do not repeat applying sunscreen during exposure to the sun.

UV radiation level changes continuously, because of latitude, air pollution, season, clouds, and other factors. Therefore, it is very difficult to give accurate, reliable and timely warnings to the public about the UV radiation levels for specific location and day time. The only practical means that the public can use to defend itself is a personal measuring device.

Another problem is that the effectiveness of sunscreen lotions that decrease gradually due to perspiration, absorption and mechanical contact. The efficiency is also reducing as a function of the time pass since manufacturing. The public does not know how much to apply and when to reapply sunscreen. All sunscreens, which are transparent, block only part of the UV spectrum (until 360 nm), since there is also a pick in the UVA range (see the action spectrum graph), that is not blocked, and the user is left unprotected while assuming full protection.

A dosimeter was disclosed and described in U.S. Pat. No. 6,132,681 by the inventor of the present invention. The dosimeter disclosed in this application comprises a polymeric matrix with embedded therein a photochromic compound combine with UV absorber with effective gradient capable of changing its original color after exposure to UV radiation with efficacy corresponding to at least 1 MED.

There is a known-in-the-art disposable dosimeter for sun radiation as per Shiseido Co.'s U.S. Pat. No. 4,829,187. This dosimeter employs a photo sensitive composition consisting of a discoloring agent, a photo activator and a UV-ray absorber. The photo activator forms free radicals by the irradiation of UV rays and the discoloring agent exhibits a color change in the visible region of a spectrum through the action of free radicals and a UV-ray absorber. The disadvantage of this dosimeter is associated with the fact that its principle of operation, and therefore the compound employed therein, is neither suitable to measure the radiation dose which is equivalent to MED, nor is it selective to different types of the user's skin. The known dosimeter is designed in such a manner, that the amount of UV-radiation necessary for inducing the color change can be 1-100 J/cm.sup.2. These values are far away from the magnitude of UV-radiation corresponding to an MED, which is about 20 mJ/cm.sup.2 for skin type no. 2.

Also known is a method and device for monitoring UV radiation as disclosed in Cybrandian Ltd.'s U.S. Pat. No. 5,117,116. In the specification of this patent it is mentioned that to facilitate quantifying the minimum dose of UV radiation an individual can tolerate, the dose of UV radiation which induces reddening in the skin is referred to as the Minimum Erythemal Dose. This dosimeter employs a chemical compound capable of changing its color on being subjected to UV radiation reflected from the skin of the user. The principal disadvantage of this provision is associated with the fact that various types of skin in various conditions reflect differently and therefore cause enormous uncertainty in the determining of the actual dose of UV radiation to which the skin of an individual has been subjected irrespective of whether this dose is attributed as an MED or not. Furthermore, there is no mention in the specification of the above patent how the outside temperature might influence the performance of the chemical compound. Since for monitoring reflected radiation the dosimeter should be provided with a dedicated support means capable of directing the reflected radiation upon the chemical compound the dosimeter's construction is complicated and inconvenient to use.

There is known a sunburn dosimeter as disclosed in American Cyanamid Co.'s U.S. Pat. No. 3,903,243. The principle of operation of this dosimeter is based on comparing the color change of a test area bearing chemical compounds capable of changing their color depending on the cumulative exposure to UV radiation with a standard area. The standard area bears a chemical compound which changed its color after exposure to different predetermined quantities of sunburn radiation. Unfortunately, the chemical compounds employed in this dosimeter are not chosen depending on their sensibility to a radiation, the amount of which is equal to an MED. These compounds are chosen depending on their capability for coloration after exposure to radiation referred to arbitrary time units and assuming that there exists a linear relationship between the ultimate time of exposure and the skin type. This assumption is not correct from the medical point of view. It should also be mentioned that comparison of a test area with a standard area is inevitably subjective and therefore renders the dosimeter less accurate.

Furthermore, there is known an ultraviolet radiation dosimeter as per Trumble's U.S. Pat. No. 3,787,687. The principle of operation of this dosimeter is similar to the previously mentioned dosimeter and is based on the comparison of a standard color chart with the color of a chemical compound exposed to UV radiation. The chemical compounds employed in this dosimeter are not chosen deliberately depending on their sensitivity to an MED of radiation or to skin type.

Thus, one can see that despite the existence of various UV indicators and dosimeters there is still a need for a new, convenient, accurate and versatile measuring device which is both capable of giving timely and unequivocal and continues warning to the user about the amount of UV radiation to which he has been exposed and which also can be used for industrial and agriculture applications.

SUMMARY OF THE INVENTION

It is an object of the present invention to provide a new and improved disposable device, that is simple, cheap, and convenient as well as suitable for personal protection from the sun or for industrial, agriculture and anti counterfeiting applications.

A further object of the present invention is to provide a disposable device employing active photochromic and color changing agent that continuously and irreversibly changes the device color, and finish the color change after exposure to the predetermine dose of UV sun's or artificial source radiation.

Still, a further object of the invention is to provide a device formed as a disposable sticker or combine onto a package, wristband or other shape, which can be conveniently be used either by people or to be used in industry or agriculture applications.

The present measuring device indicates to the user to terminate exposure to the sun/artificial source of radiation after the whole device color has changed its initial color to the reference color that appears on the package, or on the device. This color signifies that the user/product/package have already been exposed to the predetermine UV dose. The device also give continues indication on UV dose exposure up to minutes, even if the irradiation is not continues.

It is therefore provided in accordance with a preferred embodiment of the present invention, a disposable device for measuring UV radiation comprising: a matrix;
at least one photochromic compound provided to said matrix wherein said photochromic compound is capable of changing its color when exposed to UV radiation;
color changing agent distributed within said matrix, wherein said color changing agent irreversibly changes the device's color as a function of the UV dose irradiated;
whereby said device is not affected by ambient conditions and visible light.

Furthermore and in accordance with another preferred embodiment of the present invention, said at least one photochromic compound is selected from a group consisting of: spiropyrans, spiroxazines derivatives, naphtospiropyranes derivatives and bis-imidazoles derivatives:

Furthermore and in accordance with another preferred embodiment of the present invention, said color changing agent is selected from the group of aromatic ketone.

Furthermore and in accordance with another preferred embodiment of the present invention, the device further comprising an organic dye that is selected from a group consisting of derivatives of phyalocyaninie, quinacridone, isoindolinone, perylene, anthraquinone, thioxanthone etc or a combination thereof, wherein said organic dye is added to the matrix to improve the color change effect.

Furthermore and in accordance with another preferred embodiment of the present invention, said photochromic compound, and said color changing agent are homogeneously distributed within said matrix.

Furthermore and in accordance with another preferred embodiment of the present invention, said matrix is formed as a thin layer made by printing or casting, or sheet made by extruding or molding having a thickness of 0.005-5 mm, and having said photochromic compound present in the amount of 0.001-1 weight percent and color changing agent in the amount of 0.001-2 weight percent therein.

Furthermore and in accordance with another preferred embodiment of the present invention, said matrix is a solid transparent polymeric layer or sheet.

Furthermore and in accordance with another preferred embodiment of the present invention, formed as a disposable sticker, badge or the like, includes a means for attaching the measuring device to a user/product, or as wristband.

Furthermore and in accordance with another preferred embodiment of the present invention, formed as a printed part of a package, covered by opaque layer or by folding and used to prevent counterfeiting or to alert a user if the package was opened previously.

Furthermore and in accordance with another preferred embodiment of the present invention, said matrix is a transparent polymeric material selected from a group consisting of polystyrenes, polyolefin's, polyester derivatives, polyvinyl chloride, cellulose derivatives, polyurethane, silicone resins, and combinations of varnishes, epoxy resins, taken alone or in combination thereof.

Furthermore and in accordance with another preferred embodiment of the present invention, said matrix is a sheet formed by extruding or molding and can endure temperature of up to 220 C, or film made by casting or printing.

Furthermore and in accordance with another preferred embodiment of the present invention, said matrix is made from such polymer that allows absorbing of sunscreen applying on the device surface, by which its possible to simulate the sunscreen effect on a user's skin.

DETAILED DESCRIPTION OF THE PREFERRED EMBODIMENTS

The present invention provides a new and unique measuring device for UV radiation. Since the device in accordance with the present invention functions as a measuring device and not as a detector or indicator, it is very important that the measuring device will be attached to the user's skin/clothing or to the product/plant in such a manner that it absorbs the same amount of UV radiation as that of the user/product.

The specific photochromic or color changing agent employed in the measuring device of the present invention are selected in such a manner that they are sensitive only to solar radiation in the UV region, or to artificial UV source.

Figure 1:
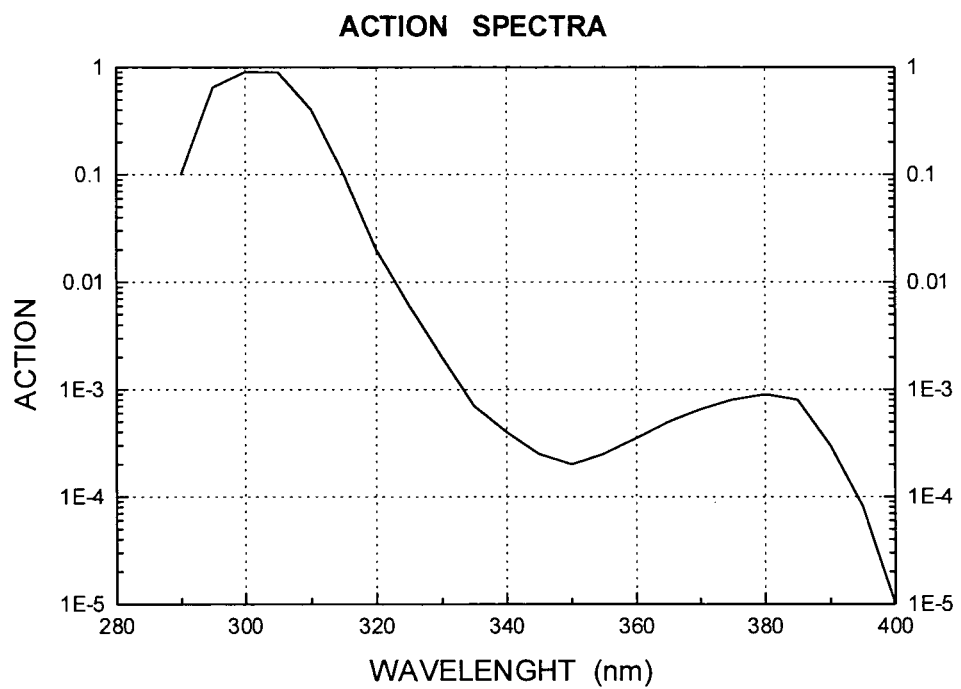
FIG. 1 illustrates example of an action spectra graph (prior art).
Figure 2:
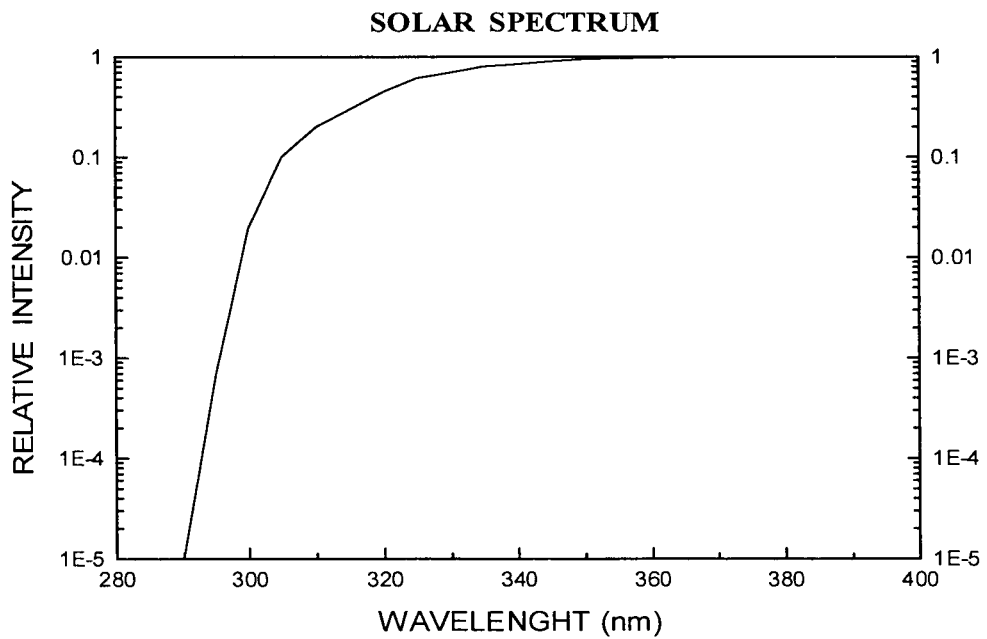
FIG. 2 illustrates the relative intensity of UV solar radiation versus wavelength (prior art).
Figure 3:
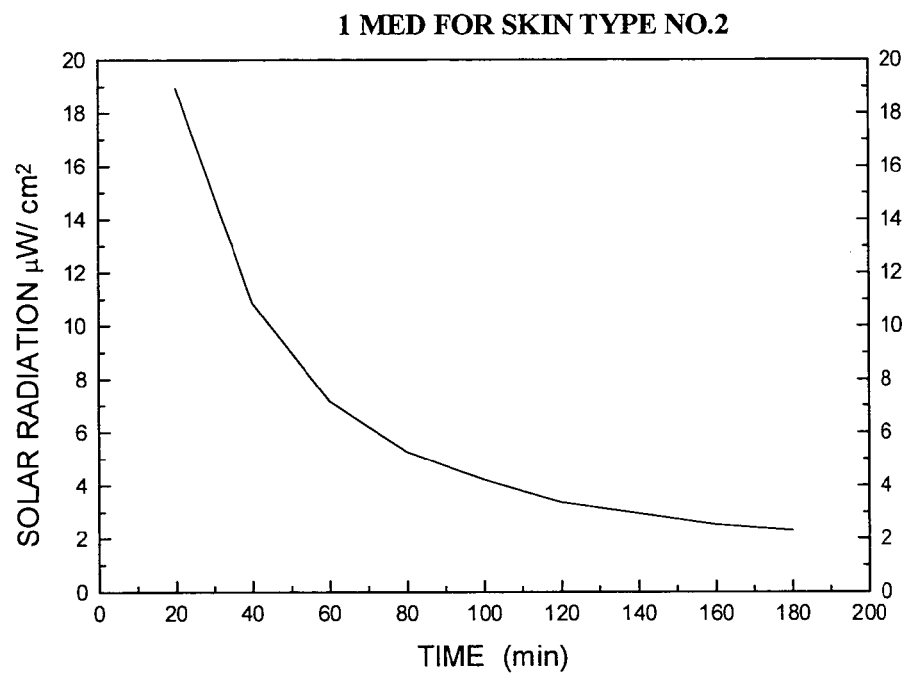
FIG. 3 graphically illustrates solar radiation efficacy as a function of time. The graph refers to skin type No. 2 and corresponds to 1 MED monochromatic radiation with wavelength 297 nm.

The amount of UV radiation that can present danger to an individual exposed to the sun's radiation is determined on the basis of existing action spectra and available data for each skin type. An average integral of the intensity of radiation vs. time is calculated from the MED efficacy-time dependence available for monochromatic radiation of 297 nm. An example of this dependency referring to skin type No. 2 is shown in FIG. 3.

For the personal applications the dose needed is set by using digital dosimeter calibrated to the measure MED sun radiations (type PMA2000 data logger with a PMA2101 UVB detector, manufactured by Solar Light co.), as a reference.

For this purpose individual samples of 10 square cm are subjected to sun radiation so as to induce change of color with/without sunscreen in parallel with the digital measuring device. The irreversibility of color and the influence of ambient temperature are tested in full spectrum of the sun's radiation.

For other applications, the desire dose is determined by the manufacture/farmer, and the measuring device is predetermined accordingly. For example the printing industry is using UV lamp to cure (dry) ink. The UV lamp intensity is decreasing in non-linear manner, and it is useful to have a fast way to check if the lamp is still affective. The best way according to a preferred embodiment of the present invention is to put a few stickers across the paper roll and run it throw the machine. Then, compare the sticker color to a reference color—if the color is not the correct one after passing under the lamp, the lamp must be replaced.

Another applications are used to prevent counterfeiting of products, or to alert if package has been opened, which could indicate that the original product was replaced or damaged. The user can be alerted by exposing the previously covered attached/combined device on the package to UV radiation and observe the irreversible color change in known time. For example, a farmer that buys seeds and would like to know that they are the original brand, can expose a printed part of the package (which is covered until then), to the sun for a few minutes and know by the irreversible color change, and then knows that he bought the original brand.

The particular combination of an photochromic compound, the color changing agent compound and the type of the matrix used in the measuring device is chosen in such a manner that the measuring device changes color during exposure to the predetermine dose of UV radiation according to the application, for example the dose which exceeded the individual's permissible MED corresponding to his personal skin type. The particular efficacy is defined for a particular skin type, by virtue of this provision the user can choose the measuring device which is safest for him and thus avoid damage to his skin and/or his eyes.

The new device operates continuously irrespective of whether it is exposed either to direct or reflected UV radiation, or if there is interruption in the irradiation thus, there will be increased awareness of the danger of cumulative exposure to UV radiation.

The device for personal use is calibrated to work simultaneously with a sun screen by applying it to the device surface, and thus increase the permissible time of exposure to the UV radiation, and insuring its safety.

Figure 4:
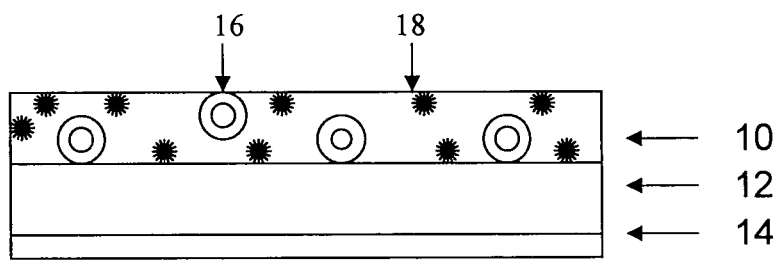
FIG. 4 illustrates structure of a new measuring device that can be worn by a user as a sticker or wristband in accordance with a preferred embodiment of the present invention.

Reference is now made to FIG. 4 illustrating the structure of a new measuring device that can be worn by a user as a sticker or wristband in accordance with a preferred embodiment of the present invention. The device for human use, the patch version, comprises a polymeric matrix made of two layers 10 and 12 (the opaque bottom layer is use to make homogenous background), with a third layer 14 attached thereto. Third layer 14 is made of a sticky material, for example, glue or scotch and by virtue of this provision the device can be attached to the user's skin, clothing or equipment. Optionally, for the wristband version this third layer is not needed, however, a sticky patch can be use in the end of the wristband for closing. The aim of matrix 10 is to carry an active chemical compound 16, to reliably protect it from corrosion due to ambient humidity and to thereto mechanical impact. Matrix 10 should be a material that is thermally stable, i.e., should not alter its character after heating up to 50 degrees C. so as to retain its transparency sufficient for visualizing the variation of color of an active compound incorporated in the matrix. The matrix also has capability to absorb sunscreen like the skin. As an example of a suitable matrix material, one can use various optically transparent materials such as, polystyrenes, polyolefin's, polyvinyl derivatives, polyester derivatives, cellulose derivatives such as cellulose acetate, polyurethanes, polyethylene; silicone resins such as LSR (liquid silicone rubber), different varnish, epoxies etc. Within the matrix an active photochromic and a color changing compound is distributed. The principle of choosing of the active compounds in accordance with the present invention will be explained further. A color changing agent is added to matrix 10. The total thickness of the matrix layers lies between 0.01-5 mm.

Figure 5:
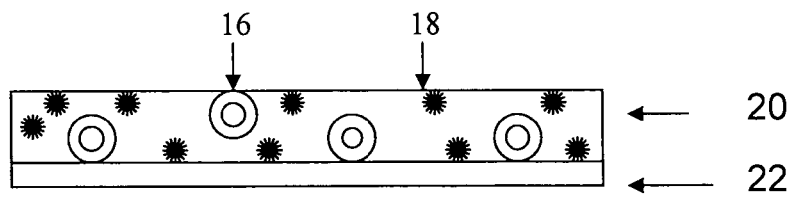
FIG. 5 illustrates structure of a new measuring device in accordance with a preferred embodiment of the present invention to be used in the industry, agriculture or as anti counterfeiting label.
Figure 6:
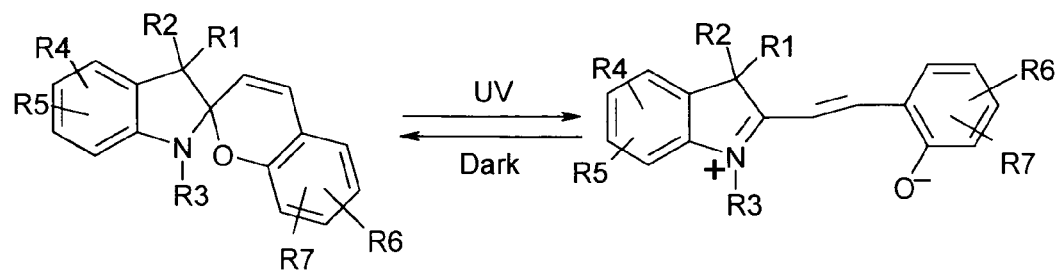
FIG. 6 illustrates the general reaction of photochemical dissociation of photochromic compound.
Figure 7:
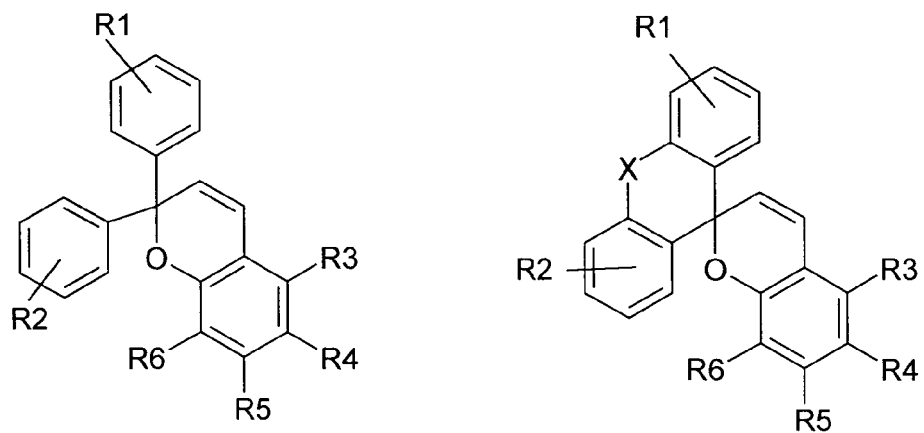
FIG. 7 illustrates the chemical formula of spiropyrans suitable for use in a measuring device in accordance with a preferred embodiment of the present invention.
Figure 8:
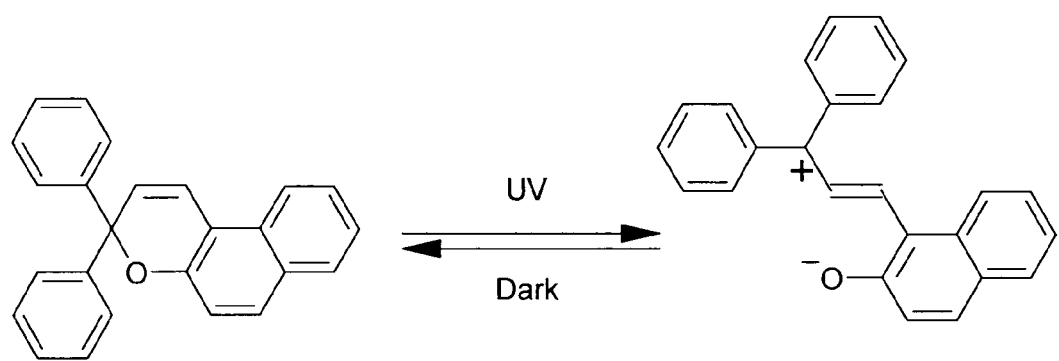
FIG. 8 illustrates the chemical formula of Naphthapyrans suitable for use in a measuring device in accordance with a preferred embodiment of the present.

Reference is now made to FIG. 5 illustrating the structure of a new measuring device in accordance with a preferred embodiment of the present invention to be used in the industry, Agriculture or as anti counterfeiting label. For industrial and agriculture applications, the sticker can be comprised of two layers: one with the active compounds 20 and second one with is the sticky layer for attachment 22.

The active compound and absorbing material can be incorporated within the matrix by means of any known-in-the-art suitable method, for example by extruding, molding, casting or printing. In practice, the amount of the photochromic 16 within the matrix and the color changing agent 18 varies between 0.001 to 2 weight percent depending on the matrix material, type of an active compound and desire sensitivity. In some case there is a need to use more then one photochromic compound in order to get more colors or colors changes.

Optionally and advantageously, it is possible to add an organic dye to the polymeric matrix in order to add suitable initial color to the measuring device which could strengthen the contrast with the color of the active material after it has been exposed to the UV radiation. Examples of such organic pigments suitable for this purpose include Pthalocyanine, Quinacridone, Isoindolinone, Perylene, Anthraquinone, etc.

Having explained the construction of the new device it will now be explained in more details how the chemical compounds employed therein are chosen in accordance with a preferred embodiment of the present invention. It has been empirically established that those photochromic and UV sensitive compounds which satisfy the following criteria can be advantageously employed in the device according to the present invention:

1. The photochromic compound should be capable of undergoing color change in response to UV radiation and endure temperatures of up to 220 C during manufacturing.
2. The color change agent should be capable of irreversible color change in the sense that it should not change or reverse the photochromic compound color after it has been exposed to the predetermine UV radiation. The irreversibility of color should remain irrespective of whether the Device was exposed to visible sun radiation, held in darkness, or exposed to temperatures up to 50 degrees C., and endure temperatures of up to 220 C during production.
3. The mechanism of photochemical reaction should be one mechanism chosen from the group including, radical dissociation, or formation of complexes.

Some non exhaustive representative examples of color change agents and active photochromic compounds that satisfy the above criteria are listed below:
a) Aromatic derivatives for example as described in Margerum, J. D.; Miller, L. J.; Saito, E.; Mosher, H. S.; Brown, M.; Hardwick, R. J. Phys. Chem., 66, 2434 (1962) or in. Sousa, J. A.; Weinstein, J. J. Org. Chem., 27, 3155 (1962) or in Bluhm, A. L.; Weinstein, J.; Sousa, J. A. J. Org. Chem., 28, 1989 (1963).
b) Spiropyran derivatives represented by the general formula shown in FIG. 9. In the above formula R and/or R.sub.1 represent an alkyl group, a nitro group or a halogen. For example as described in Berman, E.; Fox, R. J. Am. Chem. Soc, 81, 5605 (1959). The chemical reaction governed by the formation of ions is presented with reference to FIG. 9.

The present invention will now be disclosed with reference to non limiting examples:

Example No. 1

The measuring device is designed for skin type No. 3 and has a total thickness of 2 mm. The matrix is manufactured in the form of a PE sheet by extruding. Distributed within this layer is 0.02 weight percent of an active photochromic material, 1',3'-dihydro-1'-(3-fluorobenzyl)-3',3'-dimethyl-6-nitro-spiro {2H-1-henzopyran-2,2'-(2H)-indulu} and 0.1 weight percent changing color agent 4-methylacetophenone. The measuring device changes color from transparent to blue after exposure and finally to yellowish after 3 MED The measuring device was irradiated by the sun during different day hours and during different seasons. The tests were calibrated by a PMA2100 data logger with a PMA2101 UVB detector manufactured by the Solar Light Co. The measuring device's color was influenced neither after having light being held on it without time limitation or being held in darkness for at least 4 hours, nor at the temperature 50 deg. C.

Example No. 2

The measuring device is designed for testing printing drying UV lamp has a total thickness of 0.005 mm. The matrix is manufactured by printing on PP film. Distributed within this layer is 0.05 weight percent of an active photochromic material, 1',3'-dihydro-1'-(3-fluorobenzyl)-3',3'-dimethyl-6-nitrospiro {2H-1-henzopyran-2,2'-(2H)-indulu} and 0.5 weight percent changing color agent 4-methylacetophenone.

The measuring device changes color from transparent to blue after exposure and finally to yellowish exposure of 0.2 second to 2500 MW UV lamps assemble in flaxo printing machine.

Example No. 3

The measuring device is designed for preventing counterfeiting of seeds is printed on the package with a thickness of about 0.01 mm, covered by opaque layer. The matrix is manufactured by printing on PP film. Distributed within this layer are 0.08 weight percent of an active photochromic material, 1',3'-dihydro-1-(3-fluorobenzyl)-3',3'-dimethyl-6-nitrospiro {2H-1-henzopyran-2,2'-(2H)-indulu} and 0.7 weight percent changing color agent 4-methylacetophenone.

When the cover is removed by scratching and exposing it to sun, the printed part will irreversible change its color from blue to clear in a few minutes.

It should be appreciated that the present invention is not limited to the above-described embodiments and that changes and modifications can be made by one ordinarily skilled in the art without deviation from the scope of the invention, as will be defined in the appended claims. The measuring device of the present invention can be used for measuring the UV dose to people and to other objects or product were exposed, for example, plants or crops in agriculture, printed items, semiconductors, etc. It should be appreciated that the features disclosed in the foregoing description, and/or in the following claims, and/or in the accompanying drawings and/or in the accompanying examples may, both separately and in any combination thereof, be material for realizing the present invention in diverse forms thereof.

Although certain presently preferred embodiments of the present invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

The invention claimed is:

1. A disposable device for measuring UV radiation comprising:
   a matrix;
   at least one photochromic compound provided to said matrix wherein said at least one photochromic compound is capable of changing its color when exposed to UV radiation and endures temperatures of up to 220° C. during production of the device; and
   a color changing agent distributed within said matrix, wherein said color changing agent is 4-methylacetophenone and said color changing agent and said at least one photochromic compound react photochemically through a mechanism of complex formation so as to form a complex capable of irreversible color change after it has been exposed to a predetermined UV radiation and endures temperatures of up to 220° C. during production of the device, and wherein the matrix is an extruded sheet or film.

2. The disposable measuring device of claim 1, wherein said at least one photochromic compound is selected from a group consisting of: spiropyrans, spiroxazines derivatives, and naphtospiropyrane derivatives.

3. The disposable measuring device of claim 1, further comprising an organic dye that is selected from a group consisting of derivatives of pthalocyanine, phyalocyanine, quinacridone, isoindolinone, perylene, anthraquinone, thioxanthone or a combination thereof, wherein said organic dye is added to the matrix to improve the color change effect.

4. The disposable measuring device of claim 1, wherein said photochromic compound, and said color changing agent are homogeneously distributed within said matrix.

5. The disposable measuring device of claim 1 wherein said matrix is film, or a sheet having a thickness of 0.1-2 mm, and having said photochromic compound present in the amount of 0.001-1 weight percent and color changing agent in the amount of 0.001-2 weight percent therein.

6. The disposable measuring device of claim 1, wherein said matrix is a solid polymeric film or sheet made from a polymeric material selected from a group consisting of polystyrenes, polyolefins, polyester derivatives and combinations thereof.

7. The disposable measuring device of claim 1, formed as a disposable sticker, badge or wristband.

8. The disposable measuring device of claim 1, wherein said matrix is made from such polymer that allows absorbance of sunscreen applied on the device surface.

9. A disposable device for measuring UV radiation comprising:
   a matrix;
   at least one photochromic compound provided to said matrix wherein said at least one photochromic compound is capable of changing its color when exposed to UV radiation; and
   a color changing agent distributed within said matrix, wherein said color changing agent is at least one aromatic ketone, wherein said color changing agent is 4-methylacetophenone and said color changing agent and said at least one photochromic compound react photochemically through a mechanism of complex formation so as to form a complex capable of irreversible color change after it has been exposed to a predetermined UV radiation, and wherein the matrix, with said at least one photochromic compound and the color changing agent therein, is a printed layer on paper or plastic.

10. The disposable measuring device of claim 9, wherein said at least one photochromic compound is selected from a group consisting of: spiropyrans, spiroxazine derivatives, and naphtospiropyrane derivatives.

11. The disposable measuring device of claim 9, further comprising an organic dye that is selected from a group consisting of derivatives of pthalocyanine, phyalocyaninie, quinacridone, isoindolinone, perylene, anthraquinone, thioxanthone or a combination thereof, wherein said organic dye is added to the matrix to improve the color change effect.

12. The disposable measuring device of claim 9, wherein said at least one photochromic compound, and said color changing agent are homogeneously distributed within said matrix.

13. The disposable measuring device of claim 9 wherein said matrix is a thin layer having a thickness of 0.005-0.5 mm, and having said at least one photochromic compound present in the amount of 0.001-1 weight percent and color changing agent in the amount of 0.001-2 weight percent therein, the matrix made from polymeric material selected from a group consisting of varnishes, inks and combinations thereof.

14. The disposable measuring device of claim 9, wherein said matrix is a solid polymeric layer.

\* \* \* \* \*